May 2, 1972 J. T. IRWIN Plant Pat. 3,149
KALANCHOE PLANT
Filed Sept. 15, 1970
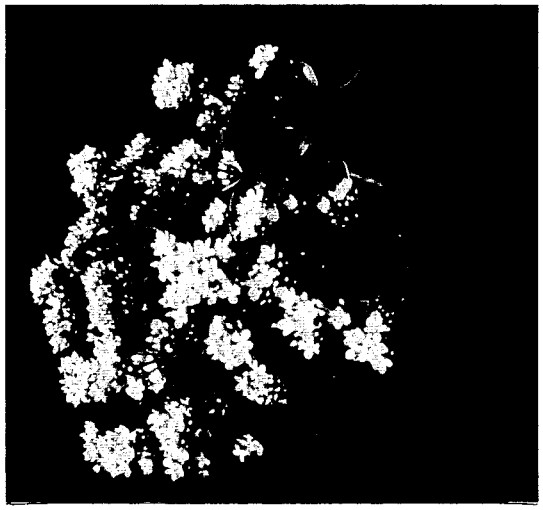
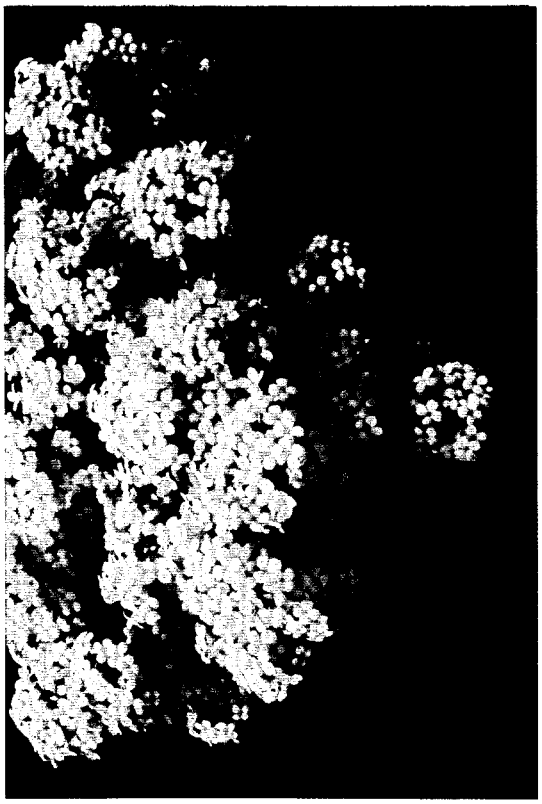
Inventor.
James T. Irwin
By: Robb & Robb
Attorneys.

United States Patent Office

Plant Pat. 3,149
Patented May 2, 1972

3,149
KALANCHOE PLANT

James T. Irwin, Canyon, Tex., assignor to Irwin Greenhouses, Inc., Canyon, Tex.

Filed Sept. 15, 1970, Ser. No. 72,557
Int. Cl. A01h *5/00*
U.S. Cl. Plt.—68 1 Claim The present invention relates to a new and distinct variety of kalanchoe plant which was discovered by me on the nursery property of my assignee located in Randall County, Tex., as a selected, cultivated seedling derived from self-pollination of plants of the Swiss hybrid kalanchoe variety known as "Exotica" (unpatented).

In the course of commercially growing the "Exotica" variety aforementioned, I had found that it was extremely variable. I, therefore, decided to conduct a program of controlled self-pollination of this variety in an effort to obtain a superior variety which was more stable and superior to other kalanchoe varieties previously available in commerce. My efforts were very successful and resulted in my selection of the new seedling which is the subject hereof and which is distinguished from its parent variety "Exotica," as well as from all other kalanchoe varieties of which I am aware, as evidenced by the following unique combination of characteristics and commercially valuable features which are outstanding in the new seedling:

(1) A highly branched, but sturdy and upright plant habit;
(2) A consistent plant height ranging between about 12 inches and 15 inches tall;
(3) Medium sized foliage of an attractive Moss Green to Fern Green color;
(4) A profuse blooming habit;
(5) A substantially uniform blooming date, but with an ability to respond to short day treatment making it capable of year-round blooming;
(6) An unusual, attractive and distinctive soft orange flower color;
(7) Long-lasting qualities as a potted plant; and
(8) An ability to initiate and develop flower buds under high night temperatures of summer when other varieties fail.

Asexual reproduction of my new kalanchoe variety by direct rooting of stem tip cuttings, as performed by me in Randall County, Tex., shows that the foregoing characteristics and distinctions come true and are established and transmitted through succeeding propagations.

The accompanying drawing shows typical specimen plants of my new kalanchoe variety, with one of said specimens being at a stage when it is beginning to bloom, and the other specimen being at a mature stage in full bloom and showing the profuse blooms on a somewhat larger scale.

The following is a detailed description of my new variety, with color terminology in accordance with the Exotica Horticultural Color Guide (Roehrs Co., Rutherford, N.J.) except where general color terms of ordinary dictionary significance are obvious:

Parentage: A selected cultivated seedling derived from controlled self-pollination of the Swiss hybrid kalanchoe variety known as "Exotica."

Propagation: Holds its distinguishing characteristics through succeeding propagations by direct rooting of stem tip cuttings.

Locality where grown and observed: Randall County, Tex.

Plant:

*Form.*—Much-branched; upright; compact; uniform height ranging from about 12 inches to 15 inches.

*Growth habit.*—Medium vigorous.

*Rooting habit.*—Numerous and fibrous; roots easily from any part of stem.

*Blooming habit.*—Compound umbel.

*Blooming season.*—Normally about December 10, but suitable for forcing into year-round bloom by manipulating long and short days under suitable greenhouse conditions.

Foliage:

*Size.*—Medium. Length—about 4 inches. Width—about 2½ inches.

*Quantity.*—Abundant.

*Color.*—New foliage—Upper side—Green, No. 83−. Under side—Green, No. 82+. Old foliage—Upper side—Green, No. 83−. Under side—Green, No. 82+. Shape—oval. Base—from obtuse to acute. Tip—obtuse.

*Texture.*—Upper side—glossy; smooth. Under side—smooth.

*Margin.*—Crenate.

Disease resistance: Superior resistance to root rot, as determined by comparison with other kalanchoe varieties grown under the same greenhouse conditions in Randall County, Tex.

Flowers: Perfect; average diameter from about ⅝ inch to ¾ inch; depth of flower from peduncle from about ½ inch to about ⅝ inch.

*Size of petals.*—Width—about ¼ inch, Length—about ⅜ inch.

*Form.*—Perigynous; section-petals united; ovary inferior.

*Color.*—Uniform. Upper side of petals—Soft Orange, No. 18−. Under side of petals—Orange, No. 16+, with throat of corolla tinged No. 4.

*Blooming period.*—From 4 to 6 weeks.

Hardiness: Good; has withstood temperatures of 35° F. in central New Mexico, and 105° F. in Canyon, Tex.

General observations: Very attractive even with only a few flowers open; flowers form a massive flower head composed of hundreds of individual flowers at maturity and retain their fresh appearance while doing so; under side of leaves take on a bronze cast under high sunlight conditions.

I claim:

1. A new and distinct variety of kalanchoe plant, substantially as herein shown and described, characterized particularly as to novelty by the unique combination of a highly branched, but sturdy and upright plant habit, a consistent plant height ranging between about 12 inches and 15 inches tall, medium sized foliage of an attractive Moss Green to Fern Green color, a profuse blooming habit, a substantially uniform blooming date, but with an ability to respond to short day treatment making it capable of year-round blooming, an unusual, attractive and distinctive soft orange flower color, long-lasting qualities as a potted plant, and an ability to initiate and develop flower buds under high night temperatures of summer when other varieties fail.

No references cited.

ROBERT E. BAGWILL, Primary Examiner